US010551391B2

(12) United States Patent
Verschoor et al.

(10) Patent No.: US 10,551,391 B2
(45) Date of Patent: Feb. 4, 2020

(54) METHOD OF DIAGNOSING TUBERCULOSIS

(71) Applicant: UNIVERSITY OF PRETORIA, Pretoria (ZA)

(72) Inventors: Jan Adrianus Verschoor, Die Wilgers (ZA); Carl Baumeister, Lynnwood Manor (ZA)

(73) Assignee: University of Pretoria, Pretoria (ZA)

( * ) Notice: Subject to any disclaimer, the term of this patent is extended or adjusted under 35 U.S.C. 154(b) by 887 days.

(21) Appl. No.: 14/891,490

(22) PCT Filed: May 15, 2014

(86) PCT No.: PCT/IB2014/061468
§ 371 (c)(1),
(2) Date: Nov. 16, 2015

(87) PCT Pub. No.: WO2014/184768
PCT Pub. Date: Nov. 20, 2014

(65) Prior Publication Data
US 2016/0169905 A1    Jun. 16, 2016

(30) Foreign Application Priority Data
May 16, 2013    (ZA) .................. 2013/03590

(51) Int. Cl.
*G01N 33/569*   (2006.01)
*G01N 33/68*    (2006.01)
*G01N 33/543*   (2006.01)

(52) U.S. Cl.
CPC ..... *G01N 33/6854* (2013.01); *G01N 33/5432* (2013.01); *G01N 33/5438* (2013.01);
(Continued)

(58) Field of Classification Search
None
See application file for complete search history.

(56) References Cited

U.S. PATENT DOCUMENTS 6,124,105 A    9/2000  Verschoor et al.
6,433,013 B1   8/2002  Verschoor et al.
(Continued)

FOREIGN PATENT DOCUMENTS

WO    2005/116654    12/2005
WO    2013/186679    12/2013

OTHER PUBLICATIONS

Thesis/Dissertation: University of Pretoria, "An assessment of two evanescent field biosensors in the development of an immunoassay for tuberculosis", published Jul. 31, 2008 (Year: 2008).*
(Continued)

*Primary Examiner* — Tracy Vivlemore
*Assistant Examiner* — Nam P Nguyen
(74) *Attorney, Agent, or Firm* — Nixon & Vanderhye, P.C.

(57) ABSTRACT

Mycolic acid antigen containing liposomes, and an electrode immobilised antigens of tuberculous mycobacterial origin are produced. A diagnostic sample from a human suspected of having tuberculosis is diluted and divided into first and second samples. A control sample comprising the first sample and a redox probe is exposed to the liposomes. A test sample comprising the second sample and a redox probe is exposed to liposomes not containing mycolic acid antigens. The control sample is contacted with the immobilised antigens to allow antibodies therein to bind to the antigens. The test sample is contacted with the immobilised antigens to allow any antibodies therein to bind to the antigens. The degree of binding in the samples is compared by electrochemical impedance spectroscopy. Any observed lesser binding by the control sample is an indicator of antibodies to the antigens in the diagnostic sample, indicating tuberculosis in the human.

13 Claims, 5 Drawing Sheets

(52) U.S. Cl.
CPC ..... *G01N 2333/35* (2013.01); *G01N 2469/20* (2013.01); *G01N 2800/12* (2013.01)

(56) References Cited

U.S. PATENT DOCUMENTS

| | | | |
|---|---|---|---|
| 6,458,367 B1 | 10/2002 | Verschoor et al. | |
| 7,122,577 B1 | 10/2006 | Verschoor et al. | |
| 7,851,166 B2* | 12/2010 | Verschoor .......... | G01N 33/5695 424/130.1 |
| 7,851,830 B2 | 12/2010 | Arnold et al. | |
| 2015/0111219 A1* | 4/2015 | Baumeister ........ | G01N 33/5432 435/7.1 |

OTHER PUBLICATIONS

Huayhuas-Chipana et al. ("Nanostructured Screen-Printed Electrodes Modified with Self-Assembled Monolayers for Determination of Metronidazole in Different Matrices", J. Braz. Chem. Soc., vol. 25, pp. 1737-1745, published 2014) (Year: 2014).*

Garcia-Gonzalez, Raquel, et al., "Electrochemical Characterization of Different Screen-Printed Gold Electrodes", *Electrochimica Acta*, 53:3242-3249 (2008).

International Search Report issued in PCT/IB2014/061468, dated Dec. 8, 2014 (3 pages).

Mathebula, Nsovo S., et al., "Recognition of Anti-Mycolic Acid Antibody at Self-Assembled Mycolic Acid Antigens on a Gold Electrode: A Potential Impedimetric Immunosensing Platform for Active Tuberculosis", *Chem. Commun.*, pp. 3345-3347 (2009).

Ozoemena, Kenneth I., et al., "Electron Transfer Dynamics Across Self-Assembled N-(2-Mercaptoethyl) Octadecanamide/Mycolic Acid Layers: Impedimetric Insights Into the Structural Integrity and Interaction with Anti-Mycolic Acid Antibodies", *Physical Chemistry Chemical Physics*, 12:345-357 (2010).

Benadie et al., "Cholesteroid nature of free mycolic acids from *M. tuberculosis*", *Chemistry and Physics of Lipids*, 152:95-103 (2008).

Diaz-Gonzalez et al., "Immunosensor for *Mycobacterium tuberculosis* on screen-printed carbon electrodes", *Biosensors and Bioelectronics*, 20:2035-2043 (2005).

Lemmer et al., "Detection of Antimycolic Acid Antibodies by Liposomal Biosensors", *Methods of Enzymology*, 464:79-104 (2009).

Schleicher et al., "Prevalence of Anti-mycolic Acid Antibodies in Patients with Pulmonary Tuberculosis Co-infected with HIV", *Clinical Chemistry and Laboratory Medicine*, 40(9):882-887 (2002).

Thanyani et al., "A novel application of affinity biosensor technology to detect antibodies to mycolic acid in tuberculosis patients", *Journal of Immunological Methods*, 332:61-72 (2008).

* cited by examiner

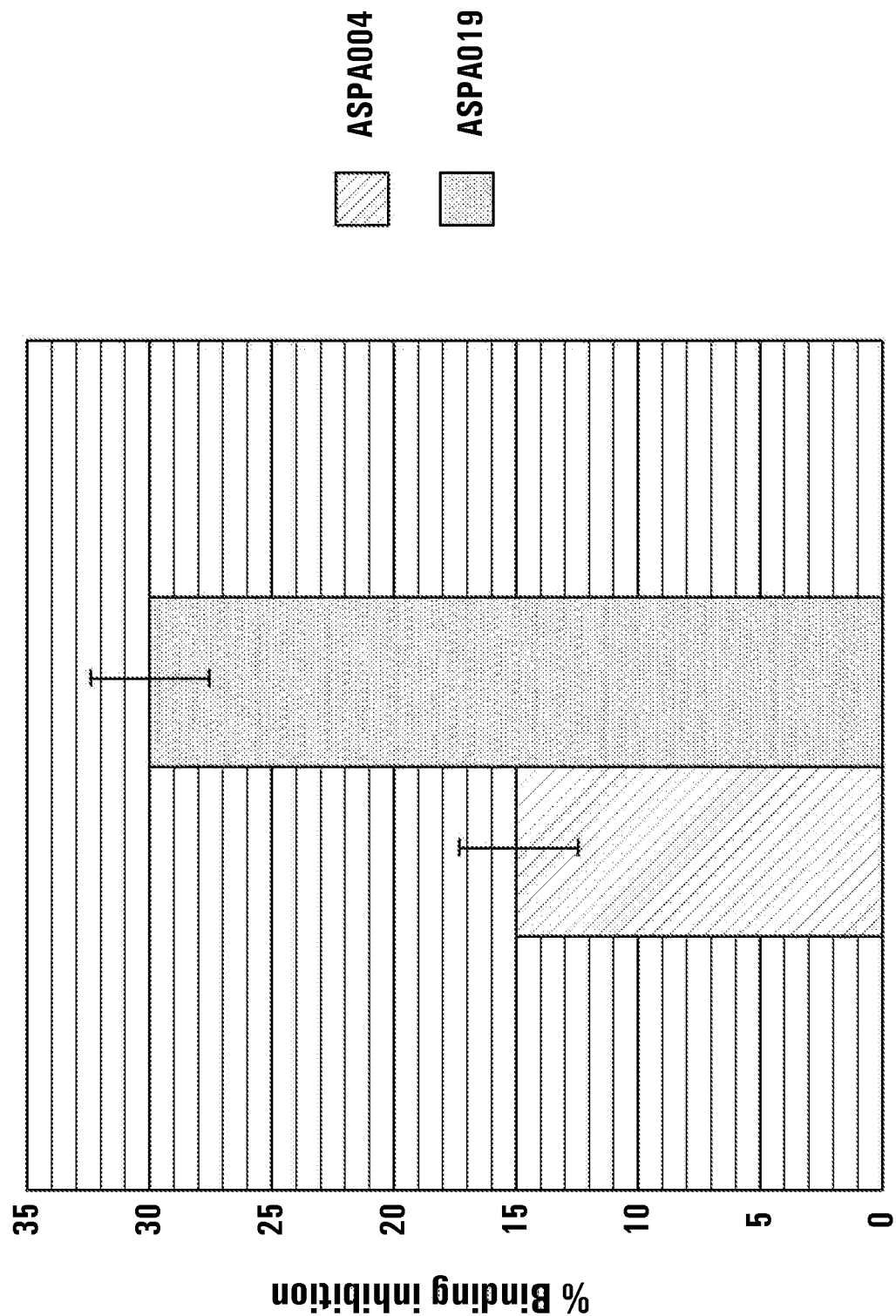

METHOD OF DIAGNOSING TUBERCULOSIS

This application is a U.S. National Phase Entry of International Application No. PCT/IB2014/061468, filed May 15, 2014, which designated the U.S. and claimed the benefit of South African Application No. 2013/03590, filed May 16, 2013. The entire contents of each of the above-identified applications are hereby incorporated herein by reference.

THIS INVENTION relates to a method of diagnosing tuberculosis. In particular, the invention relates to a serodiagnostic method for active tuberculosis (TB), based on the detection of antibodies in mammalian subjects to lipid antigens derived from *Mycobacterium tuberculosis*.

For diseases such as TB, there have to date been no commercial serological TB diagnostic test which has been effective enough to warrant its use for TB diagnosis (Weyer et al., 2011), despite the fact that much progress has been reported in studies of antibodies to various antigens of *M. tuberculosis* in the serum of patients with TB.

The present invention provides a method of diagnosing tuberculosis by the detection of surrogate marker antibodies in immunoglobulin containing body fluid samples. Surrogate markers are indicators of a disease and are produced by the host in response to the infection, rather than by the infectious agent itself.

The surrogate marker antibodies are antibodies that specifically recognise mycolic acid antigens from tuberculous mycobacteria (Verschoor et al., 1998, U.S. Pat. No. 7,122,577), and the Applicant is aware that the prevalence of such antibodies is not affected by co-infection with HIV, the virus that causes AIDS (Schleicher et al. 2002). The Applicant is also aware that antibodies can be detected by means of a competitive binding inhibition immunoassay, in order to distinguish them from the ubiquitous cross-reacting anti-cholesterol antibodies (Verschoor et al., 2005, Thanyani et al. 2008, Benadie et al. 2008). The Applicant is further aware that antibody binding to mycolic acid antigen containing liposomes immobilised on a sensor surface can be detected in real-time with biosensor technology using diluted samples, to improve sensitivity and specificity of detection compared to standard immunoassays such as ELISA (Verschoor et al., 2005, Thanyani et al. 2008, Lemmer et al. 2009). The Applicant is further aware that surrogate marker antibodies can be end-point detected on a self-assembled lipid monolayer with embedded mycolic acid antigen, using electrochemical impedance spectroscopy (EIS) (Mathebula et al. 2009, Ozoemena et al. 2010).

In the referenced prior art, the technology for the applicable diagnosis of tuberculosis has been given the acronym "MARTI", i.e. the Mycolic acid Antibodies Real-Time Inhibition test (Lemmer et al., 2009). However, the MARTI-test is challenged by requiring expensive and tedious biosensor technology, such as surface plasmon resonance, with concomitant low sample throughput and high maintenance requirements. The electro-impedance spectroscopy technique of Mathebula et al. (2009) and Ozoemena et al. (2010) was an attempt to find a method of biosensor detection of the surrogate marker antibodies that would be more amenable for practical diagnostic application. Although technically successful, it deviated from the principle of MARTI by being performed as an end-point antibody binding detection assay, for which inadequate sensitivity may be expected when validated with larger serum sample sets.

The present invention provides an improvement on the prior art by applying the electro-impedance biosensor approach to the principles of the MARTI-assay by configuring the measurement of electro-impedance in a novel way. This entails the exclusion of the washing step after antibody-antigen exposure on the electrode sensor surface and inclusion of a redox probe or similar conductive species in combination with antibody-containing samples. This arrangement enhances the sensitivity of the test by preventing the washing away of low-affinity biomarker antibody together with unbound serum components. The present invention utilises low cost, chemical solvent resistant, screen-printed, disposable electrodes that make the principles of the MARTI-test amenable for high sample throughput. In addition, the present invention provides for sequential injection of inhibited and non-inhibited samples, i.e. the exposure of the inhibited and non-inhibited samples to the same sensor surface in sequence, which permits a full analysis requiring only a single disposable electrode per sample.

Various approaches have previously been explored for the detection of TB. Biosensors based on piezo-electrics (He et al., 2002, Ren et al., 2008), DNA-binding (Das et al., 2010), magneto-elastic (Pang et al., 2008), acoustic wave (He et al., 2003) and SPR-based DNA sensors (Duman & Erhan, 2010). These innovations, however, were aimed at direct bacilli detection and do not address the washing away of low-affinity antibodies. The method of Pang et al. (2008) makes use of a sputum sample and is known to be compromised in HIV co-infected patients. There is great scientific and commercial interest in biosensors for TB detection, but none have yet offered a solution to the extra-pulmonary, paediatric and HIV co-infected populations.

Proof of principle that biomarkers of tuberculosis anti-mycolic acids antibodies can be detected using electrochemical impedance spectroscopy (EIS) was provided by Mathebula et al. (2009). EIS is essentially an analytical technique that detects changes on an electrode surface with an electric current. This publication suggests the use of a covalently linked self-assembled monolayer to form a capacitive layer including mycolic acids. However, in its current configuration the method does not allow for high sample throughput due to tedious electrode polishing and chemical methods. The Applicant has now found that screen-printed electrodes (SPEs) combined with electrochemical impedance spectroscopy can be used to detect anti-mycolic acid antibodies.

Screen-printing technology, or silk-screening, has been known for many years and has been used successfully to produce screen-printed electrodes. In the method of the current invention, gold "ink" is used on a ceramic alumina support as shown in FIG. 1 to produce a three electrode system. The gold electrodes are cured, either by high or low temperature curing as shown in FIGS. 2 and 3. This avoids the need for tedious polishing (García-González et al., 2008). In an electrode system, controlling parameters such as surface roughness and self-assembled monolayer (SAM) reproducibility are important. High throughput antibody detection requires that methods for controlling the surface roughness should be optimised to provide confidence in obtaining reproducible results.

Screen printing permits the reproducible production of high quality disposable electrodes at low cost. Being disposable is important due to the impracticality of surface regeneration for diagnostic purposes. When alternative technologies were used (e.g. the Biacore SPR biosensor) the gold surface of the cuvette had to be chemically regenerated before each analysis. This could cause etching of the surface when self-assembled monolayers (SAMs) were used. Furthermore, chaotropic agents such as urea may be present in serum; these agents have damaging effects on electrodes (Dijksma, 2003). This can destroy reproducibility and accuracy through indeterminate error. It is extremely difficult, expensive and impractical to characterise surface changes between regenerations due to these factors. Disposable SPEs present a solution to both the reproducibility and the cost.

Electrochemical impedance spectroscopy was first introduced by Oliver Heaviside in the 1880's (Barsoukov & MacDonald, 2005). About 125 years later electrochemical techniques were found suitable for monitoring binding interactions on self-assembled monolayers (SAMs) (Campuzano et al., 2006). Charge-transfer occurs via a redox probe in solution across a working, reference and counter electrode. Simply put, a constant voltage at the $E_{1/2}$ of the cell is maintained at a set of different frequencies based on the defined scan parameters. The alternating current has both amplitude and a phase angle. The change in the phase angle occurs due to changes in the system, including ion diffusion due to increased capacitance. The frequency response analysis (FRA) is measured in this assay. EIS is used to study two groups of parameters: those affecting the material such as conductivity, dielectric constant, charge mobility, equilibrium concentrations of charged species, bulk reaction rates, and those belonging to the electrode-material interface including, adsorption-reaction rate constants, capacitance on the interface region and diffusion coefficient of neutral species in the electrode itself (Barsoukov & MacDonald, 2005). SAMs form the insulating layer which restricts the charge transfer, thereby causing capacitance (Gebbert et al., 1992). Charge-transfer resistance ($R_{ct}$) at the electrolyte-SAM-working electrode interface occurs due to antibody binding via physical adsorption (Tudorache & Bala, 2007). $R_{ct}$ can be quantified using EIS techniques and will be the basis for analysis used here.

Direct label-free detection of an antibody-antigen response can be achieved by impedance measurements during potential pulses (pulsed amperometric detection). This allows for the detection of a change in capacitance and or charge transfer resistance of the electrode introduced by the binding of protein that forms an additional layer above the SAM (Berggren & Johansson, 1997).

Calibration of the system is required using cyclic voltammetry to determine the equilibrium potential ($E_{1/2}$) of the system (see FIG. 4). This value is used in EIS to measure current perturbations between the working electrode (WE) and the counter electrode (CE). An example of a counter electrode for measuring SAMs reported previously, was silver chloride and the redox probe was hexacyanoferrate or $[Fe(CN)_6]^{4-}/[Fe(CN)_6]^{3-}$ when using gold as the working electrode (Mathebula et al., 2009).

Working electrodes act as a source of electrons for exchange at the interfacial region and must be biologically inert (in other words they will not generate a current in response to an applied potential). Gold has previously been used as the working electrode due to its inert and conductive properties. It was easily conjugated with acetylcystine or any thiol, which forms a highly stable dative covalent bond between the sulphur and the gold surface. If the sulphur is part of a long-chain alkane or similar molecule it will form the insulating layer. The formation of the insulating layer must be removed if the electrode is to be re-used. This requires that the electrode must be cleaned or polished between each use. This is impractical and introduces the possibility of determinate error.

The use of disposable electrodes prevents effects of surface adsorption and damage due to excessive cleaning, thereby ultimately increasing reproducibility. The electrodes can be prepared off-site and applied in a point of care (POC) setting where electrode polishing and coating is impractical.

In an aqueous solution electrode-electrolyte interfaces can be modified with the use of SAMs consisting of hydrophobic compounds/molecules/nanoparticles attached to the electrode surface. N-(2-mercaptoethyl)octadecaneamide (MEODA) has previously been used by Ozoemena et al., 2010 and Mathebula et al., 2009 and 11-mercaptodecanoic acid (MEA) has been used by Zhang et al., 2009. The Au-MEODA-MA principle used by Ozoemena et al. (2010) involved the linking of cysteamine to gold, followed by covalent attachment of stearic acid and finally incorporation of mycolic acids by hydrophobic interactions. It was thought that this orientated the mycolic acids vertically with hydrophobic portions facing downwards and the mycolic motif and other hydrophilic groups towards the outer surface of the SAM. This allowed for binding with anti-mycolic acid antibodies, which provided the evidence needed that TB diagnostics is possible using EIS.

Previous work has shown that self-assembled monolayers (SAMs) impede the flow of current. As a gold surface is covered with long-chain alkanethiols, almost all current is blocked with dynamic resistances reported of 69 $\Omega cm^2$ for butanethiol, compared to thiocitic acid that has a lower resistance at 40 $\Omega cm^2$, which allowed the passage of the redox couple (probe) to such an extent that results were almost identical to bare gold (Berggren & Johansson 1997). Furthermore, the occurrence of this impedance has been proven to increase (using a SAM with mycolic acids) when anti-mycolic acid antibodies (Anti-MA Ab's) in a TB infected patient's serum bind to the immobilized layer of mycolic acids (Ozoemena et al., 2010, Mathebula et al., 2009). This is crucial information that provided the proof for using the EIS principle in TB diagnosis.

The standard approach to measure impedance is to apply a single-frequency voltage to the interface and measure the phase shift and amplitude of the resulting current at the specific frequency or to perform fast Fourier transform analysis of the response (Barsoukov & MacDonald, 2005). FIG. 5 depicts the Randle's equivalent circuit which is used to construct the Nyquist plot.

A visual representation of cyclic voltammetry and EIS helps to understand first principles. FIG. 4 shows the effects of conjugation of a complexed SAM onto a gold electrode. As the surface becomes derivatized by the hydrophobic component, the flow of current decreases and the shape changes from sigmoidal (a) to less sigmoidal (b) to elliptical (c). Here one must assume linear function and observe that the potential drop (E) is equal to the current (I) multiplied by the solution resistance ($R_s$).

$$E = I \times R_s$$

This means that if the E and the $R_s$ are kept constant as the SAM is formed (and insulation increases) the current will decrease. In EIS this will be visualised as an increase in the size of the semicircle of the Nyquist plot and therefore an increase in $R_{ct}$ (see FIG. 5 and FIG. 6).

Thus, according to the invention, there is provided a method of diagnosing tuberculosis by detecting a surrogate marker for active tuberculosis, the method including the steps of taking up isolated mycolic acid antigens of tuberculous mycobacterial origin or a synthetic analogue thereof in a liposome carrier to produce mycolic acid antigen containing liposomes;

immobilising isolated mycolic acid antigens of tuberculous mycobacterial origin or a synthetic analogue thereof on an electrode to produce immobilised antigens of tuberculous mycobacterial origin on the electrode;

obtaining a diagnostic sample from a human or animal suspected of having active tuberculosis, which sample may contain surrogate marker antibodies to the immobilised mycolic acid antigens;

diluting some or all the diagnostic sample and dividing some or all of the diluted sample into a first and a second sample;

producing a control sample by combining the first sample with a redox probe and exposing the control sample to the mycolic acid antigen-containing liposomes;

producing a test sample by combining the second sample with the redox probe and exposing the test sample to liposomes not containing mycolic acid antigens;

contacting the control sample with the immobilised mycolic acid antigens to allow any antibodies in the control sample to bind to the immobilised mycolic acid antigens;

contacting the test sample with the immobilised mycolic acid antigens to allow any antibodies in the test sample to bind to the immobilised mycolic acid antigens; and comparing the degree or extent of the binding of the antibodies to the immobilised mycolic acid antigens in the control sample and the test sample by electrochemical impedance spectroscopy, any observed lesser binding shown by the control sample being due to the presence of antibodies to the mycolic acid antigens in the diagnostic sample indicating active tuberculosis in the human or animal from which the diagnostic sample originated so that active tuberculosis is thereby diagnosed in the human or animal.

The liposomes have lipid bilayer membraneous nanostructures which are used to hold or contain the lipid antigens, which in the present invention is mycolic acid. The diagnosis of the human or animal may be effected within 24 hours from obtaining the diagnostic sample, preferably on the same day as that on which the sample is obtained. This is an important advantage of the invention since many prior art diagnostic procedures are lengthy and laborious.

The immobilisation of the mycolic acid antigens may be by direct binding thereof to a self-assembled monolayer in combination with a binding agent or a polymer, to obtain a mycolic acid antigen containing self-assembled monolayer on the electrode. The self-assembled monolayer may comprise a thiolated hydrophobic substance. The thiolated hydrophobic substance may be octadecanethiol.

The electrode may be a screen-printed electrode. The mycolic acid antigen containing self assembled monolayer may be in the form of a coating on a surface of the screen-printed electrode. A self-assembled monolayer is a layer of compounds or molecules attached to a surface and which, under the right conditions, form spontaneously.

The method may include forming the mycolic acid antigen-containing self-assembled monolayer by exposing the electrode surface to the hydrophobic substance initially and thereafter exposing it to the mycolic acid antigens. Instead, the method may include forming the mycolic acid antigen-containing self-assembled monolayer by exposing the electrode surface to a mixture of the hydrophobic substance and the mycolic acid antigens.

The control sample and the test sample may be sequentially contacted with the immobilised antigens of the same screen-printed electrode. Instead, the control sample and the test sample may be separately contacted with the immobilised antigens of separate screen-printed electrodes. In the former case, the test sample substitutes the control sample on the screen-printed electrode during sequential contact with the immobilized antigens. The test sample may be pumped onto the surface and simply displaces the control sample without the requirement of any intermediate washing steps. In other words, no washing of the screen-printed electrode between the contacting thereof with the control sample and the contacting thereof with the test sample is required. This is an important advantage of the present invention. Where the control sample and the test sample are separately contacted with the immobilised antigens of separate screen-printed electrodes, the samples may be contacted with the separate electrodes at the same time.

As indicated hereinbefore, the diagnostic sample may contain surrogate marker antibodies to the immobilised mycolic acid antigens. In other words, if the human or animal from whom the diagnostic sample is obtained has active tuberculosis, the diagnostic sample will contain surrogate marker antibodies to the immobilised mycolic acid antigens.

Combining the first and second samples respectively with the redox probe may be effected in a buffer solution. The redox probe with which the first and second samples are combined may be the same.

The mycobacterial infection may be of the type which causes diseases selected from pulmonary and extra-pulmonary tuberculosis. The mycolic acid antigen may be extracted from *Mycobacterium tuberculosis* and the antibodies may be antibodies against *Mycobacterium tuberculosis* or antibodies against mycolic acid components thereof. The mycolic acid antigens may be in a form selected from homogeneous and heterogeneous compound mixtures.

The sample of human or animal origin may be selected from blood samples, spinal fluid samples and samples that naturally contain antibodies. The sample may be from an HIV positive human. In particular the antibodies may be low affinity antibodies.

The exposure of the control sample and the test sample to the immobilised isolated mycolic acid antigen may include pre-incubating the control sample with the liposomes containing mycolic acid antigens and pre-incubating the test sample with the liposomes not containing mycolic acid antigens.

In the method of the invention, the screen-printed electrodes may be briefly polished, and coated in ODT-hexane to form the self-assembled monolayer, followed by a wash in absolute ethanol. Mycolic acid in hexane may then be applied, followed by another ethanol wash. The screen-printed electrode may then be characterized by cyclic voltammetry (in redox probe solution) to determine the $E_{1/2}$ and then EIS (frequency response analysis) may be performed to determine the baseline. In the "control step" the inhibited sample, i.e. diluted serum sample with mycolid acid (MA) containing liposomes and redox probe may be pumped onto the surface, thereby displacing the redox probe solution from the first step. The "control step" solution may then be allowed to bind for a brief fixed period and then analysed by EIS. In the "test step" the "control step" solution may be displaced by the "test step" solution i.e. diluted serum sample with MA-free liposomes and redox probe which may be pumped onto the electrode surface. This exposes the electrode to the "test step" solution for a brief fixed period as in the previous step. The signal may then be analysed a third time, after binding has occurred. The difference between the inhibited and non-inhibited sample is compared. If the difference is substantial, the patient is considered TB positive.

The invention also provides a test kit for use in diagnosing tuberculosis by detecting surrogate marker antibodies indicating active tuberculosis, the kit including one or more screen-printed electrodes, isolated mycolic acid antigen of tuberculous mycobacterial origin or a synthetic analogue thereof, buffer forming reagents, redox probe forming reagents and liposome forming reagents.

The invention is now illustrated, by way of example, with reference to the following Figures and the accompanying non-limiting example in which FIG. 1 shows Dropsens™ [Llanera (Asturias), Spain] screen-printed electrodes without and with insulating layer with a conductive layer (a) and an insulating layer (b);

Figure 1:
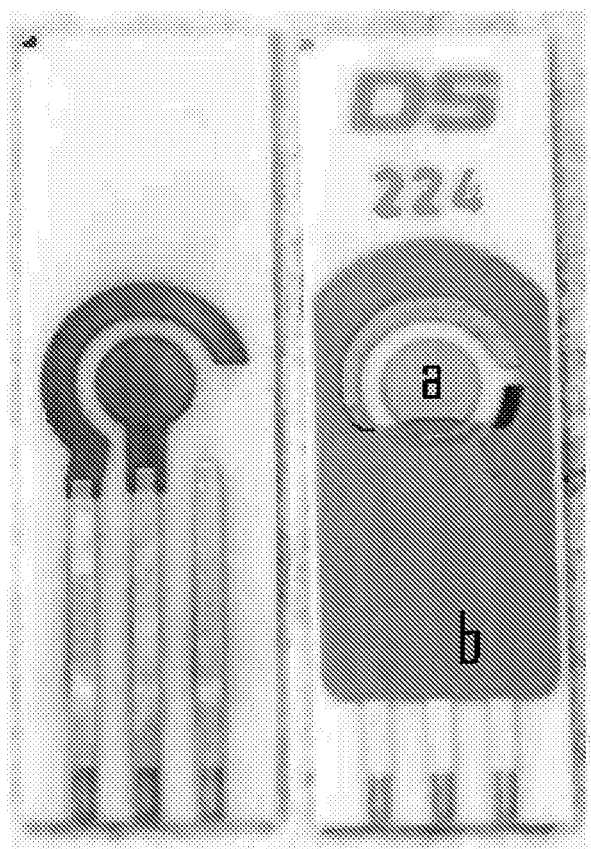
Figure 2:
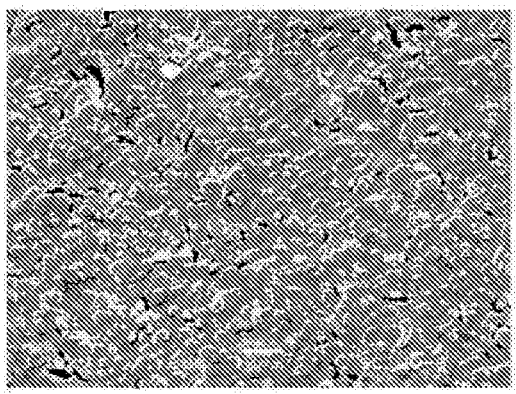
FIG. 2 shows scanning electron microscope images of "ink" cured at high temperature on screen-printed electrodes (Dropsense™ Screen-Printed Gold Electrodes catalogue)
Figure 3:
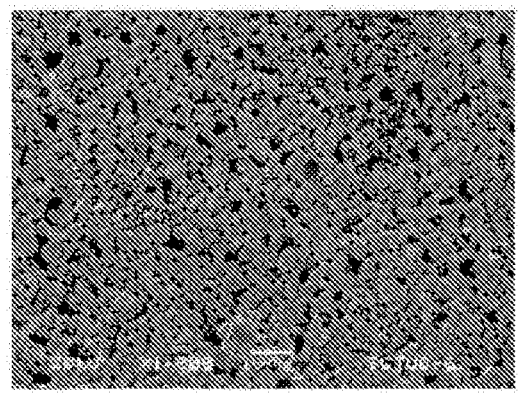
FIG. 3 shows scanning electron microscope images of "ink" cured at low temperature on screen-printed electrodes (Dropsense™ Screen-Printed Gold Electrodes catalogue)
Figure 4:
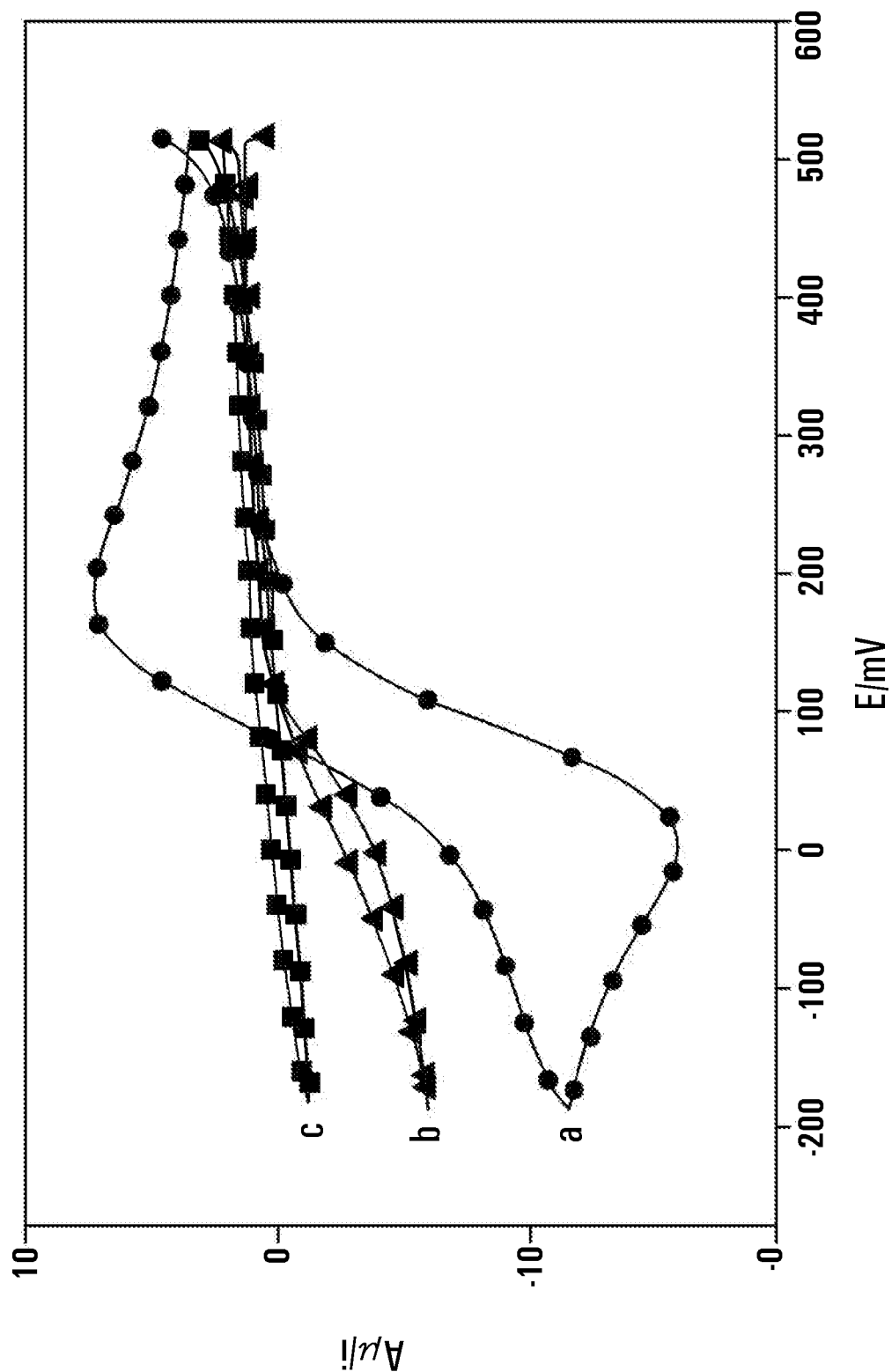
Figure 5:
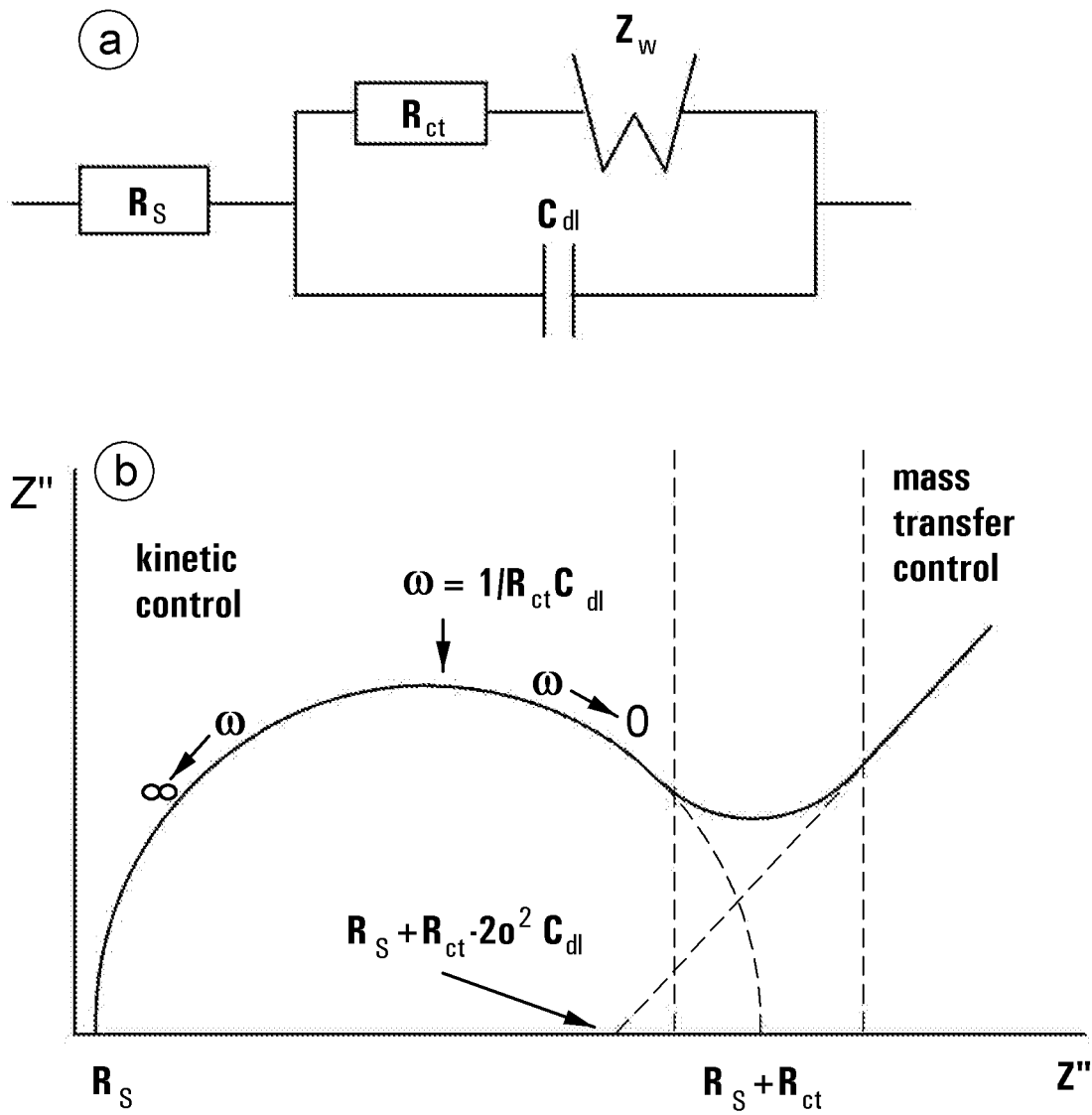

FIG. 4 shows a typical cyclic voltammogram of potential (E) in millivolts (mV) against current (i) in micro Amperes (pA) for the binding of a complexed SAM onto a gold electrode in 5 mM $K_3[Fe(CN)_6]$ solution at a scan rate of 10 mV/s; (a) gold plus thiocitic acid, (b) gold plus thiocitic acid plus antibody, (c) gold plus thiocitic acid plus antibody plus 1-dodecanethiol (Berggren & Johansson 1997);

FIG. 5 shows a Randle's equivalent circuit (a) which describes the response of a single-step charge-transfer process with diffusion of reactants and/or products to the interface and its associated Nyquist plot (b); $C_{dl}$ is the capacitance of a double layer, $R_s$ is solution resistance, $R_{ct}$ is charge transfer resistance (speed of electron transfer), and $Z_w$ is Warburg impedance (electrolyte resistance); for the Nyquist plot (b). Z' is real frequency and Z" is imaginary frequency. The positive slope at mass transfer control is during the diffusion process (linear or radial) (Dijksma, 2003, Barsoukov & MacDonald, 2005, p 70)

Figure 6:
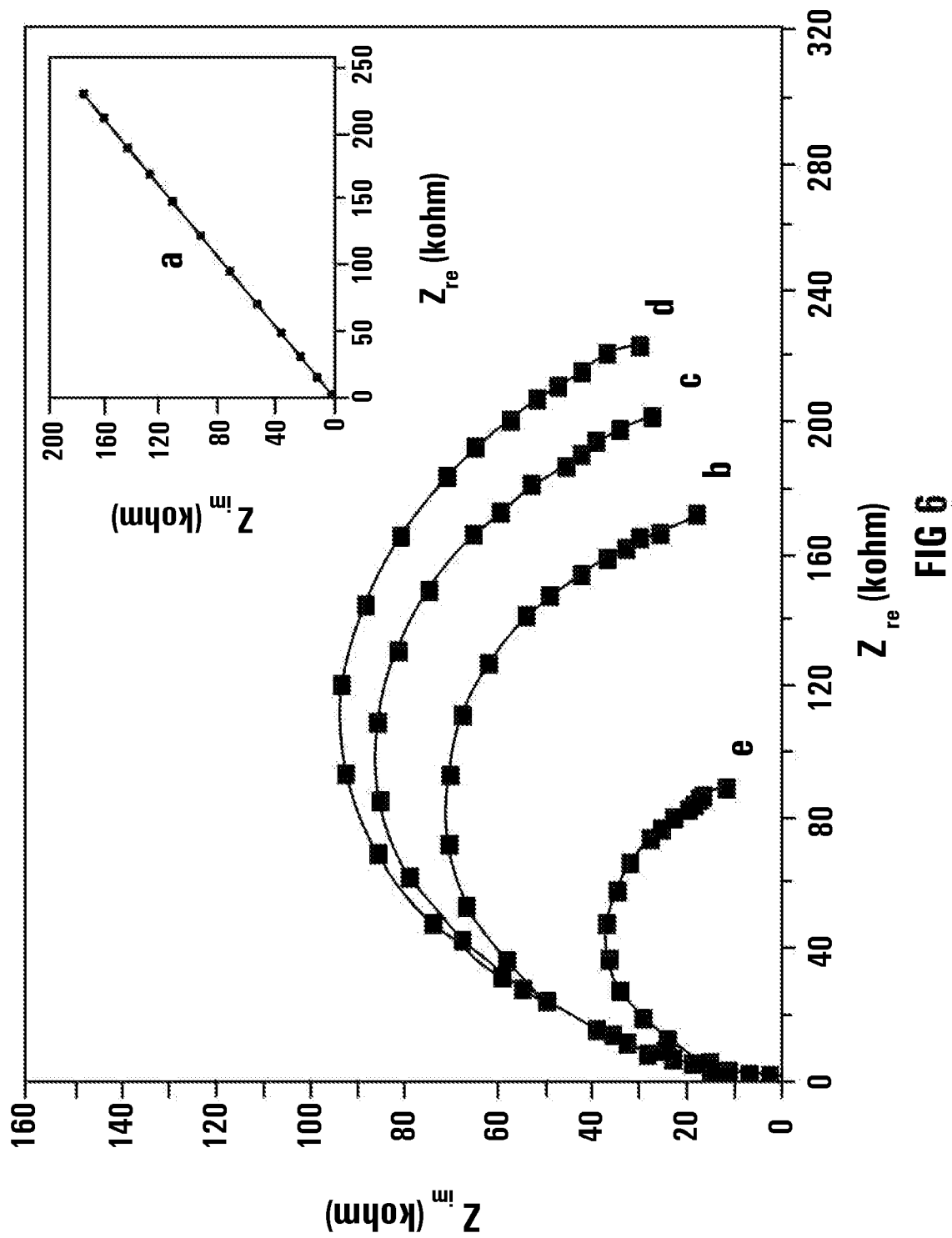

FIG. 6 is a Nyquist plot ($Z_{imaginary}$ against $Z_{real}$) showing an increase in $R_{ct}$ during immobilsation steps of (a) electrodeposition of gold layer (b) assembly of 11-MUA monolayer (c) immobilization of anti-human IgG (d) binding of human IgG antigen (e) regeneration (Zhang et al., 2009);

FIG. 7 shows mean values of percentage binding inhibition of TB negative (ASPA004) and TB positive (ASPA019) patient sera using solvent resistant electrodes. Error bars represent the standard deviation, n=4.

EXAMPLE 1

Detection of Low Affinity Anti-Mycolic Acids Antibodies
Materials
(1) Mycolic acids were purchased from Sigma Aldrich, Germany. Assay reagents were purchased from Sigma. Ethanol, acetone, chloroform, hexane and dimethylformamide were purchased from Merck South Africa.
(2) PBS buffer (20×) consisted of: 160 g NaCl, 4 g KCl, 4 g $KH_2PO_4$, 4 g anhydrous $Na_2HPO_4$, dissolved in 1 litre $dddH_2O$. PBS/AE buffer (1×): 0.25 g $NaN_3$ and 0.3802 g EDTA were dissolved in 50 ml 20×PBS buffer and 800 ml $dddH_2O$, adjusted to pH 7.44 with 1 M acetic acid and made up to a final volume of 1 litre with $dddH_2O$, before filtering through 0.22 µm filter disc using a Solvac® filtration system.
(3) A 1 mM solution of hexacyannoferrate (Ferri/Ferrocyanide) i.e. $[Fe(CN)_6]^{4-}/[Fe(CN)_6]^{3-}$ (from Bio-zone Chemicals, South Africa) was made up in 1×PBS/AE buffer. Analysis was done using an Autolab PGstat302 (Autolab, the Netherlands) with the GPES and FRA software.
(4) The blood samples collected from HIV positive patients were delivered freshly to the laboratory for serum preparation. Samples were kept at 15° C. before they were processed within eight hours after sampling. After the blood clotted (2-4 hours after sampling), serum was removed from the blood clot using plastic Pasteur pipettes and transferred to 1.5 ml Eppendorf tubes. The serum samples were then centrifuged in a microfuge (360 g, 5 minutes, 4° C.) to remove any cellular matter still present. The serum samples were then aliquoted (500 µL portions) into 1.8 ml cryotubes (NUNC© Brand products, Nunc international, Denmark) and stored at −70° C. When an adequate number of samples were obtained in this way, they were thawed once more and γ-irradiated (30 Gy, 5 minutes on each side of the box, Pretoria Academic Hospital) as a safety precaution (Vermaak, 2005), in order to inactivate any viral activity. From this step, samples were finally frozen at −70° C. until used for MARTI-analysis. Here, a MARTI positive (ASPA019) and a MARTI negative control (ASPA004) were used.
Methods
(1) Electro-analysis: Bare screen-printed electrodes [DRP-220AT, Dropsens, Llanera (Asturias), Spain] were briefly polished, rinsed in hexane and characterized in 0.1 mM Ferri/Ferrocyanide in PBS/AE (the redox probe solution). Cyclic voltammetry was performed between a window potential of −0.336 V to 0.6 V with a step potential of 0.00244 V and a scan rate of 0.025 V/s. This allowed for the determination of the $E_{1/2}$ of each specific electrode in the flow cell. By performing a peak search the $E_{1/2}$ was found to be about 0.15 V. The analysis was performed using the EIS (frequency response analysis) on FRA software (Metrohm Autolab, the Netherlands) at the $E_{1/2}$ of the cell from 2 kHz to 1 Hz.
(2) Electrodes were then coated with a 0.1 M ODT-hexane solution, rinsed in absolute ethanol and then coated in 40 µl of a 0.5 mg/ml MA-hexane solution. This was washed with absolute ethanol again and then analysed to determine the baseline using the EIS technique at the $E_{1/2}$ mentioned in (1).
(3) Serum samples were diluted and incubated with liposomes to produce a "control step" solution and a "test step" solution.
Inhibition studies were performed using a patient serum that was left at room temperature to thaw completely. A 20 minute pre-incubation of 1/500 dilutions of serum with solutions of liposomes containing mycolic acids "control step" or liposomes not containing mycolic acids "test step" was allowed. These were then sequentially injected for binding inhibition studies to the electrode surface. Control and test solutions were allowed to bind for 10 min as can be seen in (4) and (5) respectively.
(4) "Control step". After incubation the inhibited sample (the diluted serum sample with MA containing liposomes and redox probe in PBS/AE buffer) was pumped onto the surface, which displaced the redox probe solution. The "control step" solution was allowed to bind for a brief fixed period and then analysed by EIS.
(5) "Test step": The "control step" solution was then displaced by the "test step" (non-inhibited sample) i.e. the serum sample that had not been exposed to antigen and in which antibody binding activity remains maximal. The signal was analysed a third time, after binding was allowed to occur over the same time as in (4). The difference between the inhibited and non-inhibited sample was compared.
(6) If a substantial signal difference between the control and test samples was detected the patient was considered TB positive.

RESULTS AND DISCUSSION

Patients with active TB will exhibit increased levels of antibodies to mycobacterial cell wall mycolic acids. The antibodies have previously been detected by various techniques including ELISA, waveguide and resonant mirror biosensors. Results with ELISA published by Schleicher et al. (2002) provided 57% accuracy. With the resonant mirror biosensor 82% accuracy was achieved for detection biomarker anti-mycolic acids antibodies (Thanyani et al., 2008). The Applicant has now shown that the principles of an inhibition assay in the MARTI assay as described by Verschoor et al. (2005) can be applied to detect a response by means of an amperometric technique, namely electrochemical impedance spectroscopy (EIS). The ability to distinguish between TB-positive and TB-negative sera occurs as a result of a difference in bound antibody to a surface.

To investigate if the principles of MARTI could be incorporated into the EIS system the Applicant investigated the addition of the redox probe to the serum dilution, together with either the inhibiting or non-inhibiting liposomes. In theory this would be expected to eliminate the need for a washing step after antibody exposure, thereby retaining the ability to detect the binding of low affinity biomarker antibodies. The liposomes were made as described (Thanyani et al., 2008), but a redox probe containing PBS/AE (0.1 mM Ferri/Ferrocyanide in PBS/AE) was used as the suspension liquid. The serum dilutions and liposomes were prepared in the presence of the redox probe. The PBS/AE buffer containing the redox probe was also used during the inhibition step and during measurements after immobilisation onto the electrode surface. A second measurement was performed after exposure of non-inhibited serum sample to the sensor surface. This sample comprised of serum, redox probe, PBS/AE buffer and liposomes not containing MA. Without being limited thereto, the Applicant believes that this could take place by a mechanism in which unbound antibodies and liposomes from the "control step" are removed from the electrode simultaneous with injection of the "test step" solution. The Applicant also believes that the method of the invention can be automated.

The difference between TB-negative and TB-positive serum was observed by a difference in percentage inhibition of antibody binding to sensor surface immobilized MA calculated from $R_{ct}$ values. In this instance, an increase in charge transfer resistance was an indicator of antibody binding to mycolic acids on the surface. This occurred due to the formation of an immuno-complex of immobilized antigen (mycolic acids) and antibody from the serum sample. Because the mycolic acids were immobilised in the SAM across the electrode surface, the immune-complex lowered the capacitance by increasing the distance between the outer layer and the electrode, and thereby increased the resistance to charge transfer ($R_{ct}$). This hindered the interfacial electron transfer kinetics at the electrode-electrolyte interface (Hays et al., 2006).

The data from FIG. 7 indicated a near 50% difference in signal between TB-positive and TB-negative sera that was statistically significant. This represented the degree to which anti-mycolic acid antibodies bound to the sensor surface in TB-infected serum. The results suggested that for the purpose of TB diagnostics, antibody binding to mycolic acids using SPEs can only be used for MARTI TB testing purposes if the solvent resistant SPEs are used that were designed specifically for the purpose of this invention.

In conclusion, Mathebula et al. (2009) and Ozoemena et al. (2010) paved the way for the use of EIS in TB serodiagnosis, providing the groundwork and principles. The Applicant has now shown that a high sample throughput diagnosis can be achieved by alleviating tedious electrode polishing, costly electrodes and complex carbodiimide surface chemistry. Previously an EIS TB test based on anti-MA antibody detection could take up to one week. The method of the present invention allows this time to be cut back to one day using screen-printed electrodes, with the potential to decrease this to under an hour. Screen-printed electrodes have been used previously in an attempt to diagnose TB (Diaz-Gonzalez et al., 2005). Their system made use of carbon screen-printed electrodes, an enzyme-dependent sandwich assay, highly diluted serum sample (1:10 000) and 2×90 minute incubation steps. Their potential time to diagnosis is longer and limited to detecting high affinity antibodies because of the necessity to separate free from bound antibodies by means of a wash step. Limited published information pertains to solvent resistant electrodes for immunosensors. In 1997, Kröger & Turner investigated the use of solvent resistant carbon screen-printed electrodes for the detection of hydrogen peroxide. Potyrailo et al. (2004) used solvent resistant electrodes to assess polymer-solvent interactions. The Applicant is, however, not aware of the application of solvent resistant screen-printed electrodes for the diagnosis of TB.

The invention thus provides a real-time antibody detection method. A real time detection method means the actual time during which an antibody binds to antigen and the event is recorded. For the MARTI diagnostic this terminology refers to the detection of antibody binding to immobilised antigen at any time during the process without the need to wash away any excess of unbound antibody. In the present invention as opposed to surface plasmon resonance biosensors that allow the continuous recording of antibody binding to immobilized antigen over time, EIS measures antibody binding at particular time stamps after exposure to antigen, but still does not require a washing step to remove unbound antibody to enable recording of the events.

The method of the invention accordingly provides a novel approach for tuberculosis diagnostics and the Applicant is of the view that the method may lead to point-of-care devices for TB diagnostics.

BIBLIOGRAPHY

Barsoukov, E., Macdonald, J. R., 2005. Impedance spectroscopy theory, experiment and applications (Second Edition), Chapter 3. Measuring techniques and data analysis, McKckubre M. C. H, Macdonald, D. D., (Eds.) John Wiley & Sons Inc. (USA).

Benadie, Y., Deysel, M., Siko, D. G. R., Roberts, V. V., Van Wyngaardt, S., Thanyani, S. T., Sekanka, G., Ten Bokum, A. M. C., Collett, L. A., Grooten, J., Baird, M. S., Verschoor, J. A., 2008. Cholesteroid nature of free mycolic acids from *M. tuberculosis*. Chemistry and Physics of Lipids 152, 95-103.

Berggren, C., Johansson, G., 1997. Capacitance Measurements of Antibody-Antigen Interactions in a Flow System. Analytical Chemistry 69, 3651-3657.

Campuzano, S., Pedrero, M., Montemayor, C., Fatás, E., Pingarrón, J. M., 2006. Characterization of alkanethiol-self-assembled monolayers-modified gold electrodes by electrochemical impedance spectroscopy. Journal of Electroanalytical Chemistry 586, 112-121.

Das, M., Sumana, G., Nagarajan, R., Malhotra, B. D., 2010. Zirconia based nucleic acid sensor for *M. tuberculosis* detection. Applied Physics Letters 96, 133703-133706

Díaz-González, M., González-García, M. B., Costa-García, A., 2005. Immunosensor for *M. tuberculosis* on screen-printed carbon electrodes. Biosensors and Bioelectronics 20, 2035-2043.

Dijksma, M., 2003. Development of electrochemical immunosensors based on self-assembled monolayers, PhD Thesis, Farmacie. Universiteit Utrecht, Utrecht.

Duman, M., Erhan, P., 2010. Detection of *Mycobacterium tuberculosis* complex and *Mycobacterium gordonae* on the same portable surface plasmon resonance sensor. Biosensors and Bioelectronics 26, 2, 908-912.

García-González, R., Fernández-Abedul, M. T., Pernía, A., Costa-García, A., 2008. Electrochemical characterization of different screen-printed gold electrodes. Electrochimica Acta 53, 3242-3249.

Gebbert, A., Alvarez-Icaza, M., Stoecklein, W., Schmid, R. D., 1992. Real-time monitoring of immunochemical interactions with a tantalum capacitance flow-through cell. Analytical Chemistry 64, 997-1003.

Hays, H. C. W., Millner, P. A., Prodromidis, M. I., 2006. Development of capacitance based immunosensors on mixed self-assembled monolayers. Sensors and Actuators B: Chemical 114, 1064-1070.

He, F., Zhao, J., Zhang, L., Su, X., 2003. A rapid method for determining *M. tuberculosis* based on a bulk acoustic wave impedance biosensor. Talanta 59, 935-941.

He, F., Zhang, L., Zhao, J., Hu, B., Lei, J., 2002. A thickness shear mode immunosensor for detection of *M. tuberculosis* with a new membrane material. Sensors and Actuators B: Chemical 85, 284-290.

Kröger, S., Turner, A. P. F., 1997. Solvent-resistant carbon electrodes screen printed onto plastic for use in biosensors. Analytica Chimica Acta 347, 9-18.

Lemmer, Y., Thanyani, S. T., Vrey, P. J., Driver, C. H. S., Venter, L., van Wyngaardt, S., ten Bokum, A. M. C., Ozoemena, K. I., Pilcher, L. A., Fernig, D. G., Stoltz, A. C., Swai, H. S., Verschoor, J. A., 2009. Detection of antimycolic acid antibodies by liposomal biosensors, Methods in Enzymology 464, 79-104.

Mathebula, N. S., Pillay, J., Toschi, G., Verschoor, J. A., Ozoemena, K. I., 2009. Recognition of anti-mycolic acid antibody at self-assembled mycolic acid antigens on a gold electrode: A potential impedimetric immunosensing platform for active tuberculosis. Chemical Communications 23, 3345-3347.

Ozoemena, K., Mathebula, N. S., Jeseelan, P., Toschi, G., Verschoor, J. A., 2010. Electron transfer dynamics across self-assembled N-(2-mercaptoethyl)octadecanamide/mycolic acid layers: impedimetric insights into the structural integrity and interaction with anti-mycolic acid antibodies. Physical Chemistry Chemical Physics 12, 345-357.

Pang, P., Cai, Q., Yao, S., Grimes, C. A., 2008. The detection of *M. tuberculosis* in sputum sample based on a wireless magnetoelastic-sensing device. Talanta 76, 360-364.

Potyrailo, R. A., Morris, W. G., Wroczynski, R. J., McCloskey, P. J., 2004. Resonant multisensor system for high-throughput determinations of solvent/polymer interactions. Journal of Combinatorial Chemistry 6, 869-873.

Ren, J., He, F., Yi, S., Cui, X., 2008. A new multi-channel series piezoelectric quartz crystal for rapid growth and detection of *M. tuberculosis*. Biosensors and Bioelectronics 24, 403-409.

Schleicher, G. K., Feldman, C., Vermaak, Y., Verschoor, J. A., 2002. Prevalence of anti-mycolic acid antibodies in patients with pulmonary tuberculosis co-infected with HIV. Clinical Chemistry and Laboratory Medicine 40, 882-887.

Thanyani, S. T., Roberts, V., Siko, D. G. R., Vrey, P., Verschoor, J. A., 2008. A novel application of affinity biosensor technology to detect antibodies to mycolic acid in tuberculosis patients. Journal of Immunological Methods 332, 61-72.

Tudorache, M., Bala, C., 2007. Biosensors based on screen-printing technology, and their applications in environmental and food analysis. Analytical and Bioanalytical Chemistry 388, 565-578.

Vermaak Y. 2005. Properties of anti-mycolic acids antibodies in human Tuberculosis patients. MSc dissertation, Faculty of Natural and Agricultural Sciences, University of Pretoria, Pretoria.

Verschoor, J. A., Lenaerts, A., Johannsen, E. (1998) A composition comprising a carrier and a purified mycobacterial lipid cell-wall component and its use in the prevention, treatment and diagnosis of disease. Patent Application no. PCT/GB98/00681; U.S. Pat. No. 7,122, 577.

Verschoor, J. A., Siko, D. G. R. & Van Wyngaardt, S. (2005). A serodiagnostic method to detect antibodies to mycolic acid in tuberculosis patients as surrogate markers for infection. International patent application no. PCT/IB2005/051548, U.S. Pat. No. 7,851,830 B1; ZA 2006/09113.

Weyer, K., Mirzayev, F., van Gemert, W., Gilpin, C., 2011. Commercial serodiagnostic tests for diagnosis of tuberculosis: policy statement, World Health Organisation. WHO/HTM/TB/2011.5.

Zhang, Y., Wang, H., Nie, J., Zhang, Y., Shen, G., Yu, R., 2009. Individually addressable microelectrode arrays fabricated with gold-coated pencil graphite particles for multiplexed and high sensitive impedance immunoassays. Biosensors and Bioelectronics 25, 34-40.

The invention claimed is:

1. A method for diagnosing tuberculosis within 24 hours of obtaining a diagnostic sample by detecting surrogate marker antibodies indicating active tuberculosis, the method comprising:

taking up isolated mycolic acid antigens of tuberculous mycobacterial origin or a synthetic analogue thereof in a liposome carrier to produce mycolic acid antigen containing liposomes;

immobilising isolated mycolic acid antigens of tuberculous mycobacterial origin or a synthetic analogue thereof on a screen-printed electrode by direct binding of the antigens to a self-assembled monolayer comprising a thiolated hydrophobic substance to produce immobilised antigens of tuberculous mycobacterial origin in the form of a mycolic acid antigen containing self-assembled monolayer coating on a surface of the electrode;

obtaining the diagnostic sample from a human or animal suspected of having active tuberculosis, which sample may contain surrogate marker antibodies to the immobilised antigens;

diluting some or all of the diagnostic sample and dividing some or all of the diluted sample into a first and a second sample;

producing a control sample by combining the first sample with a redox probe and exposing the control sample to the mycolic acid antigen containing liposomes;

producing a test sample by combining the second sample with a redox probe and exposing the test sample to liposomes not containing mycolic acid antigens;

contacting the control sample with the immobilised mycolic acid antigens to allow any antibodies in the control sample to bind to the immobilised mycolic acid antigens;

contacting the test sample with the immobilised mycolic acid antigens to allow any antibodies in the test sample to bind to the immobilised mycolic acid antigens; and without a washing step to remove unbound antibody, comparing the degree or extent of the binding of the antibodies to the immobilised mycolic acid antigens in the control sample and the test sample by electrochemical impedance spectroscopy, any observed lesser binding shown by the control sample being an indicator of the presence of antibodies to the mycolic acid antigens in the diagnostic sample indicating active tuberculosis in the human or animal from which the diagnostic sample originated so that active tuberculosis is thereby diagnosed in the human or animal within 24 hours of the obtaining step.

2. The method as claimed in claim 1, wherein the thiolated hydrophobic substance is octadecanethiol.

3. The method as claimed in claim 1, which includes forming the mycolic acid antigen-containing self-assembled monolayer by exposing the electrode surface to the hydrophobic substance initially and thereafter exposing it to the mycolic acid antigens.

4. The method as claimed in claim 1, which includes forming the mycolic acid antigen-containing self-assembled monolayer by exposing the electrode surface to a mixture of the hydrophobic substance and the mycolic acid antigens.

5. The method as claimed in claim 1, in which the control sample and the test sample are sequentially contacted with the immobilised antigens of the same screen-printed electrode.

6. The method as claimed in claim 1, in which the test sample substitutes the control sample when sequentially contacted with the immobilised antigens of the same screen-printed electrode.

7. The method as claimed in claim 1, in which the mycobacterial infection is of the type which causes diseases selected from pulmonary and extra-pulmonary tuberculosis.

8. The method as claimed in claim 1, in which the mycolic acid antigens are extracted from *Mycobacterium tuberculosis* and the antibodies are antibodies against *Mycobacterium tuberculosis*, or antibodies against mycolic acid components thereof.

9. The method as claimed in claim 1, in which the mycolic acid antigens are in a form selected from homogeneous or heterogeneous compound mixtures.

10. The method as claimed in claim 1, in which the diagnostic sample is selected from blood samples, spinal fluid samples and samples that naturally contain antibodies.

11. The method as claimed in claim 1, in which the diagnostic sample is from an HIV positive human.

12. The method as claimed in claim 11, in which the antibodies are low affinity antibodies.

13. The method as claimed in claim 1, in which the exposures of the control sample and the test sample to the liposomes may include pre-incubating the control sample with the liposomes containing mycolic acid antigens and pre-incubating the test sample with the liposomes not containing mycolic acid antigens.

* * * * *